United States Patent
Vrabec et al.

(10) Patent No.: US 11,191,974 B2
(45) Date of Patent: Dec. 7, 2021

(54) CHARGE CAPACITY EXPANDING SEPARATED INTERFACE NERVE ELECTRODE (SINE)

(71) Applicant: Case Western Reserve University, Cleveland, OH (US)

(72) Inventors: Tina L. Vrabec, Cleveland, OH (US); Jesse S. Wainright, Cleveland, OH (US); Kevin L. Kilgore, Cleveland, OH (US); Narendra Bhadra, Cleveland, OH (US); Niloy Bhadra, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 91 days.

(21) Appl. No.: 16/614,951

(22) PCT Filed: May 24, 2018

(86) PCT No.: PCT/US2018/034354
§ 371 (c)(1),
(2) Date: Nov. 19, 2019

(87) PCT Pub. No.: WO2018/217999
PCT Pub. Date: Nov. 29, 2018

(65) Prior Publication Data
US 2020/0179710 A1    Jun. 11, 2020

Related U.S. Application Data

(60) Provisional application No. 62/510,465, filed on May 24, 2017.

(51) Int. Cl.
*A61N 1/44*    (2006.01)
*A61N 1/20*    (2006.01)
(Continued)

(52) U.S. Cl.
CPC ............. *A61N 1/44* (2013.01); *A61N 1/0556* (2013.01); *A61N 1/06* (2013.01); *A61N 1/20* (2013.01);
(Continued)

(58) Field of Classification Search
CPC .......... A61N 1/44; A61N 1/0556; A61N 1/06; A61N 1/20; A61N 1/36067;
(Continued)

(56) References Cited

U.S. PATENT DOCUMENTS 10,864,373 B2 *  12/2020  Bhadra ............. A61N 1/36071
2011/0160798 A1 *  6/2011  Ackermann, Jr. .... A61L 31/048
607/46

(Continued)

FOREIGN PATENT DOCUMENTS

WO    2017062272 A1    4/2017
WO    WO-2017062272 A1 *  4/2017 ............... A61N 1/20

OTHER PUBLICATIONS

Ackermann Jr, D. Michael, et al. "Separated interface nerve electrode prevents direct current induced nerve damage." Journal of neuroscience methods 201.1 (2011): 173-176.
(Continued)

*Primary Examiner* — Catherine M Voorhees
(74) *Attorney, Agent, or Firm* — Tarolli, Sundheim, Covell & Tummino LLP

(57) ABSTRACT

A capacity-expanding separated interface nerve electrode (SINE) can be used to deliver a nerve conduction block to one or more nerves. The SINE can include a source electrode coupled to a waveform generator. The source electrode can deliver an electrical neuromodulation signal (e.g., a direct current (DC) signal) to an ionically conductive medium. The SINE can also include a vessel holding the ionically conductive medium, which can include a material that facilitates
(Continued)

a transformation of the electrical neuromodulation signal to an ionic neuromodulation signal with a high charge capacity. The SINE can also include a nerve interface that can deliver the ionic neuromodulation signal to a nerve. The SINE can be used in combination with a return electrode that is also coupled to the waveform generator.

20 Claims, 8 Drawing Sheets

(51) Int. Cl.
*A61N 1/05* (2006.01)
*A61N 1/06* (2006.01)
*A61N 1/36* (2006.01)
(52) U.S. Cl.
CPC ...... *A61N 1/36067* (2013.01); *A61N 1/36071* (2013.01)

(58) Field of Classification Search
CPC .... A61N 1/36071; A61N 1/325; A61N 1/306; A61N 1/0551; A61N 1/0436; A61N 1/36103
See application file for complete search history.

(56) References Cited

U.S. PATENT DOCUMENTS

2016/0101286 A1* 4/2016 Bhadra .............. A61N 1/36071
607/46
2018/0140849 A1* 5/2018 Oron .................... A61N 1/0558
2018/0280691 A1* 10/2018 Ackermann ........... A61N 1/306

OTHER PUBLICATIONS

International Search Report dated Sep. 7, 2018 for corresponding International Patent Application No. PCT/US2018/034354.

* cited by examiner

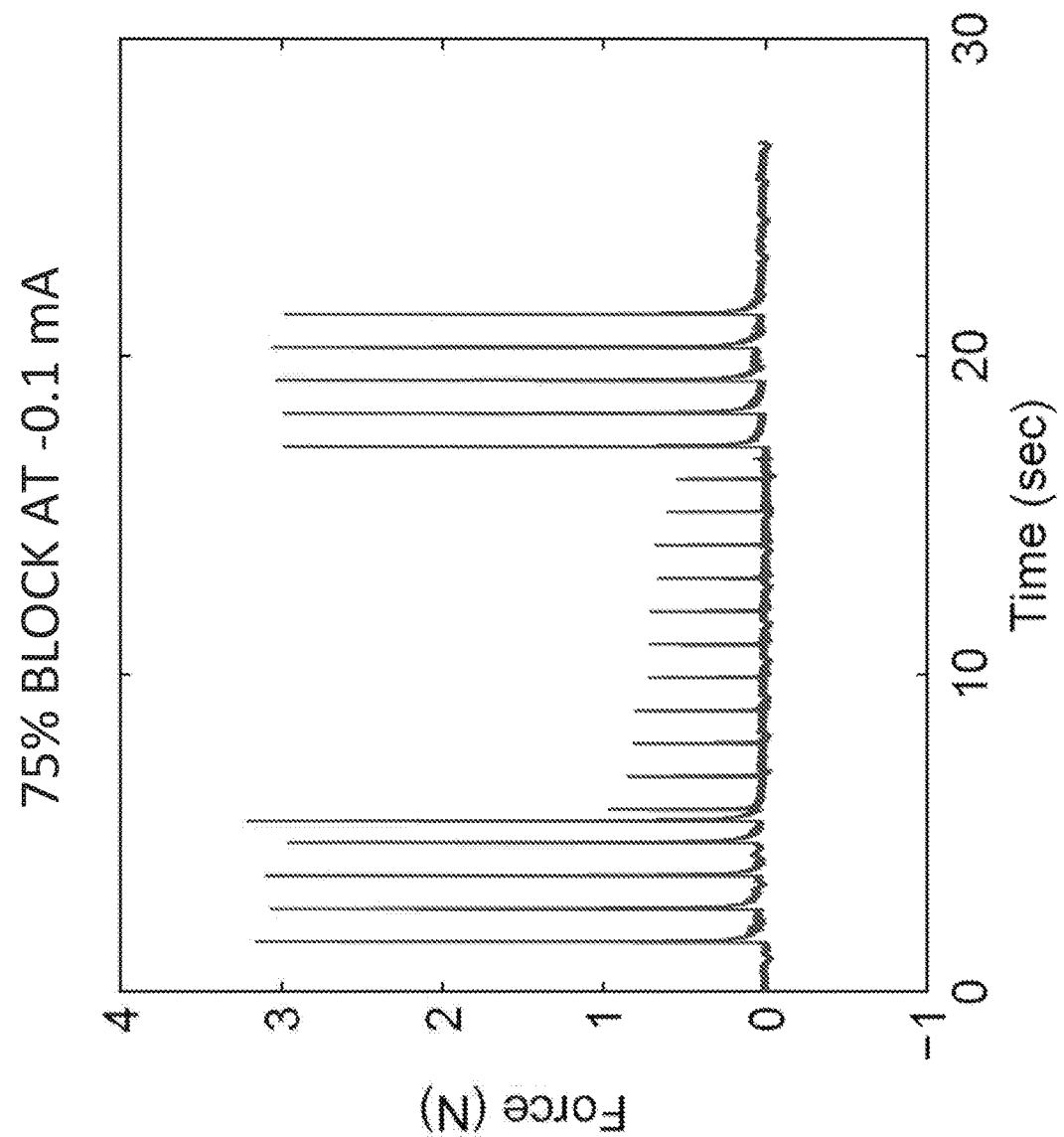

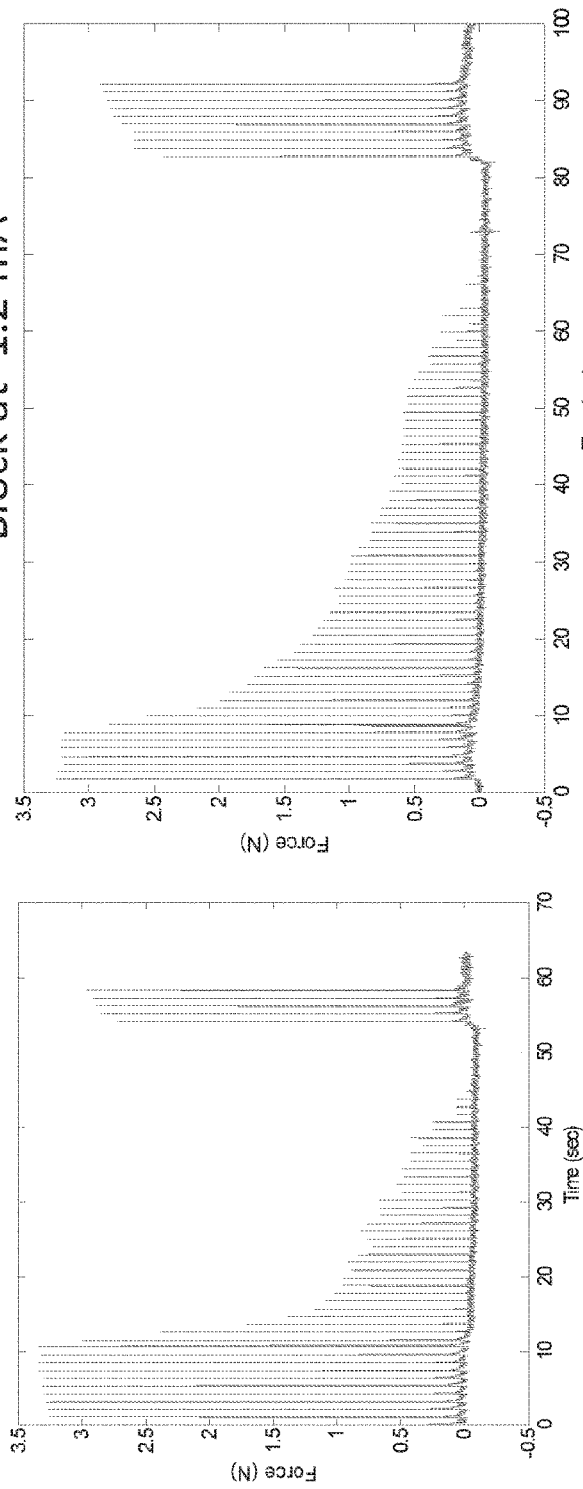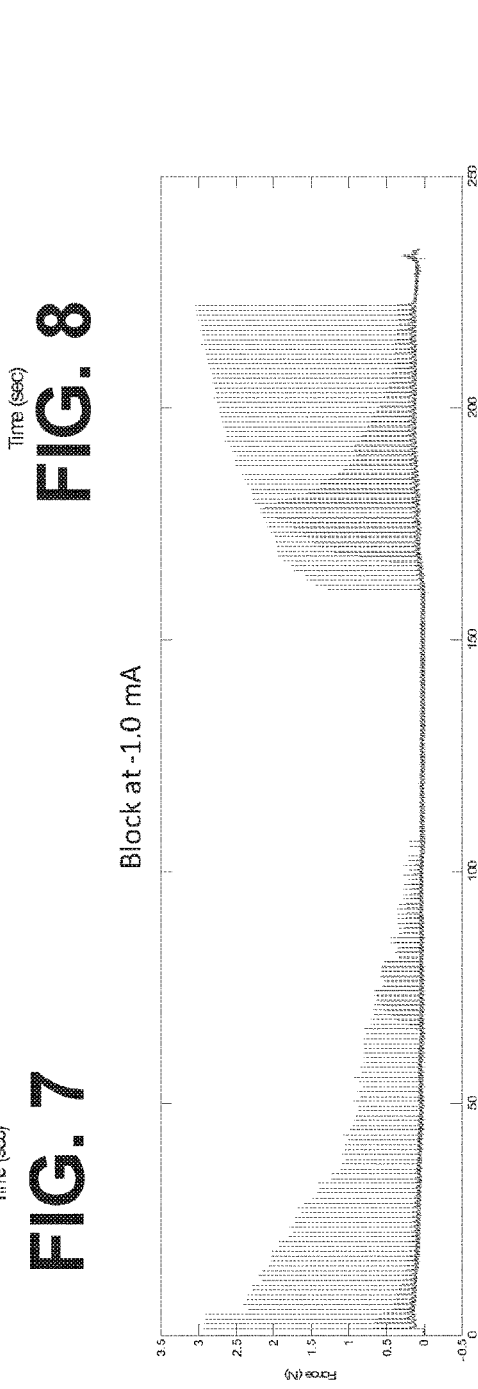

CHARGE CAPACITY EXPANDING SEPARATED INTERFACE NERVE ELECTRODE (SINE)

RELATED APPLICATION

This application claims priority to U.S. Provisional Application Ser. No. 62/510,465, filed May 24, 2017, entitled "PARTIAL POLARIZING NERVE BLOCK: CHALLENGES AND OPPORTUNITIES", the entirety of which is hereby incorporated by reference for all purposes.

TECHNICAL FIELD

The present disclosure relates generally to a charge capacity-expanding separated interface nerve electrode (SINE) and, more specifically, to systems and methods that deliver a nerve conduction block to one or more nerves as an ionic signal via the charge capacity-expanding SINE.

BACKGROUND

Many neurological disorders are characterized by unwanted neurological activity, which includes pathological effects on end organs. For example, such pathological effects can include autonomic disorders, spasticity, and chronic pain. Pharmacological methods have long been the standard for treating such pathological effects. However, such pharmacological methods have several drawbacks, including the presence side effects and interactions with other medications that limit the patients that can be treated; the inability to modulate the dosage in real time; and the like.

An alternative to the pharmacological methods is electrical nerve block, which has the capacity to provide immediate block, immediate reworkability, and real time modulation. These features allow electrical nerve block to provide personalized medicine to the patient. Kilohertz frequency alternating current (KHFAC) has been proven to provide such an electrical nerve block, but a drawback is that the application of KHFAC is preceded by a burst of spurious activity. Direct current (DC) has been shown to provide electrical nerve block without spurious activity as long as a ramp is used to bring the DC to the block threshold. Therefore, DC is generally the preferred way to deliver the electrical nerve block. However, DC is not considered "safe". Delivering the DC with a separated interface nerve electrode (SINE) can convert the electrical DC signal to an ionic signal that can be delivered to the nerve safely. However, traditional SINEs do not have the required charge capacity to deliver large DC signals safely.

SUMMARY

The present disclosure relates generally to a charge capacity-expanding SINE and, more specifically, to systems and methods that deliver a nerve conduction block to one or more nerves as an ionic signal via the charge capacity-expanding SINE. In other words, the SINE can convert an electrical neuromodulation signal to an ionic neuromodulation signal, which is delivered to one or more nerves.

In an aspect, the present disclosure can include a system that can deliver a nerve conduction block to one or more nerves via a charge capacity-expanding SINE. The system includes a waveform generator that can output an electrical neuromodulation signal (e.g., a DC signal). The system can also include a SINE that can include a source electrode, a vessel, and a nerve interface. The source electrode can be coupled to the waveform generator and can deliver the electrical neuromodulation signal from the waveform generator to an ionically conductive medium housed in the vessel. The ionically conductive medium includes a material that facilitates a transformation of the electrical neuromodulation signal to an ionic neuromodulation signal with an increased charge capacity. For example, the material can include high surface area carbon (YP-50). The nerve interface can deliver the ionic neuromodulation signal to a nerve. The system also includes a return electrode that is also coupled to the waveform generator.

In a further aspect, the present disclosure can include a method for delivering a nerve conduction block to one or more nerves via a capacity-expanding SINE. The method can include outputting an electrical neuromodulation signal (e.g., a DC waveform) by a waveform generator to a SINE. The method can also include converting, by the SINE, the electrical neuromodulation signal to an ionic neuromodulation signal. The SINE includes a source electrode that delivers the electrical neuromodulation signal to an ionically conductive medium. The ionically conductive medium can include a material that facilitates the conversion of the electrical neuromodulation signal to the ionic neuromodulation signal with high charge capacity. For example, the material can include high surface area carbon (YP-50). The method can also include delivering, by a nerve interface, the ionic neuromodulation signal to a nerve.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 6 is a plot showing a 75% block at −0.1 mA using a carbon filled SINE cuff electrode;

FIG. 7 is a plot showing a complete block at −1.6 mA using a carbon filled SINE percutaneous electrode;

FIG. 8 is a plot showing a complete block at −1.2 mA using a carbon filled SINE percutaneous electrode;

FIG. 9 is a plot showing a complete block at −1.0 mA using a carbon filled SINE percutaneous electrode;

DETAILED DESCRIPTION

I. Definitions

Figure 1:
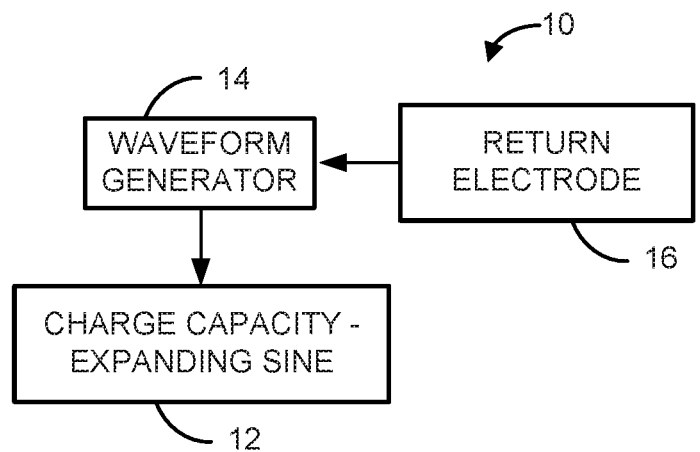
FIG. 1 is a diagram showing a system that can deliver a nerve conduction block to one or more nerves via the charge capacity-expanding separated interface nerve electrode (SINE) in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "separated interface nerve electrode (SINE)" can refer to an electrode design in which an electrode is separated from a nerve interface by a column of electrolyte. The SINE uses ionic coupling, which separates the electron flow and the ionic flow. Because the reactants of the electrochemical reaction are separated from the nerve interface, the damaging electrochemical reaction products are separated from the nerve interface. Accordingly, the SINE provides a less harmful way to deliver direct current (DC) to tissue to perform electrical block.

As used herein, the term "damaging electrochemical reaction products" can refer to chemicals produced by an electrochemical reaction that can damage the nerve, another part of the body in proximity to the electrode contact, and/or the electrode contact. For example, a damaging reaction product can be due to oxygen evolution or hydrogen evolution. As another example, a damaging reaction product can be due to dissolution of the material of an electrode contact.

As used herein, the term "electrode" refers to a conductor through which electricity enters or leaves an object, substance, or region. The electrode can, in some instances, be a high capacitance electrode. In other instances, the electrode can be a redox active electrode.

As used herein, the term "electrical block" can refer to the attenuation of conduction in at least one nerve fiber due to a change in the electric field caused by application of an electrical signal to the nerve. The terms "electrical block" and "nerve conduction block" can be used interchangeably herein. In some instances, the electrical block can provide a complete attenuation of conduction in all nerve fibers in the nerve. However, in other instances, the electrical block can provide a partial attenuation of conduction in a portion of the nerve fibers in the nerve.

As used herein, the term "electrical signal" can refer to a function that conveys information about the behavior or attributes of an electric phenomenon, such as electric current, that varies with time and/or space. For example, the electrical signal can be an alternating current (e.g., kilohertz frequency alternating current) signal and/or a direct current signal.

As used herein, the terms "direct current" or "DC" can refer to a unidirectional flow of electric charge. In some instances, the DC can have a plateau of a cathodic polarity or an anodic polarity. The DC can further be represented as a waveform that includes a ramp from a zero position to the plateau. In some instances, the waveform can also include a ramp down from the plateau position to the zero position. In still other instances, the waveform can include a subsequent plateau of the opposite polarity (in such cases, the waveform can be a biphasic waveform with the second phase configured to reduce charge either as a charge balanced waveform or a charge imbalanced waveform). The waveform can also include ramps from zero to the plateau and/or from the plateau to zero.

As used herein, the term "direct current block" or "DC block" can refer to the application of a direct current pulse with a polarity configured depolarization or hyperpolarization to cause change in the electric field sufficient to alter conduction in the nerve.

As used herein, the terms "alter" or "altering", when used with reference to nerve conduction, can refer to affecting or changing a manner in which action potentials are conducted in a nerve. In some instances, nerve conduction can be altered by extinguishing an action potential at some point as it travels along the nerve (also referred to as "blocking" nerve conduction). In other instances, nerve conduction can be altered by increasing the activation threshold of a nerve and/or decreasing the conduction velocity of a nerve (also referred to as "attenuating" nerve conduction).

As used herein, the term "neural structure" can refer to tissue related to the central nervous system, peripheral nervous system, autonomic nervous system, and enteric nervous system. The term neural structure, in some instances, can include one or more nerves and/or neural fibers.

As used herein, the term "nerve" can refer to one or more fibers that employ electrical and chemical signals to transmit information. A nerve can refer to either a component of the central nervous system or the peripheral nervous system. For example, in the peripheral nervous system a nerve can transmit motor, sensory, autonomic, and/or enteric information from one body part to another As used herein, the term "fiber" can refer to an axon of a neuron.

As used herein, the term "neurological disorder" can refer to a condition or disease characterized at least in part by abnormal conduction in one or more nerves. The neurological disorder can be in the motor system, the sensory system, and/or the autonomic system.

As used herein, the term "redox" can refer to a process in which one substance is reduce and another substance is oxidized.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "medical professional" can refer to an individual who provides care to a patient. A medical professional can be, for example, a doctor, a physician's assistant, a student, a nurse, a caregiver, or the like.

II. OVERVIEW

Traditional separated interface nerve electrodes (SINE) suffer from a low charge capacity, which limits their use for certain nerve block applications. The present disclosure relates generally to a charge capacity-expanding SINE and, more specifically, to systems and methods that deliver a nerve conduction block to one or more nerves via the charge capacity-expanding SINE. The charge capacity-expanding SINE has an increased applicability for different nerve block applications.

The charge capacity-expanding SINE can include a nerve interface separated from a source electrode by an ionically-conductive media that can facilitate the conversion to electronic current to ionic current. In some instances, the source electrode can be a high capacitance electrode in the ionically conductive medium (the non-Faradaic mode). In the non-Faradaic mode, no reactants are consumed and no reaction products are produced through the range of usage parameters defined by the waveform. The ionically-conductive media can include materials using reversible phenomena, such as (1) surface phenomena like double layer capacitance, (2) surface phenomena that involve specific adsorption (e.g., pseudo-capacitance, or (3) bulk phenomena. In other instances, the electrode can be a redox active electrode in the ionic ally conductive medium (the Faradaic mode). In the Faradaic mode, redox reactions occur, but the medium is of sufficient volume to prevent pH changes at the nerve/electrode interface. Ideally, the redox reaction can involve the uptake/discharge shuttle of biocompatible ions, such as $Na^+$, $K^+$, or $Cl^-$, to minimize or prevent any pH change or introduction of foreign ions. The redox reaction should be reversible to allow for recharge/reuse. Additionally, the redox material should be insoluble to minimize any possible contamination of the subject.

III. SYSTEMS

One aspect of the present disclosure can include a system 10 (FIG. 1) that can deliver a nerve conduction block to one or more nerves. The one or more nerves can be peripheral nerves (e.g., motor, sensory, and/or autonomic/enteric) or nerves of the central nervous system (e.g., brain and/or spinal cord). The nerve conduction block can be used to treat various neurological disorders including, but not limited to, chronic neuropathic pain or muscle spasticity. The nerve conduction block can also be used to modulate or inhibit neural activity in the autonomic or enteric system. Additionally, the nerve conduction block can be used to manage regional applications, like chronic headache management or bladder control.

The system 10 can include a charge capacity-expanding separated interface nerve electrode (SINE) 12, a waveform generator 14, and a return electrode 16. The waveform generator 14 can be coupled to the charge capacity-expanding SINE 12 and to the return electrode 16. In some instances, the coupling of the waveform generator 14 to each of the charge capacity-expanding SINE 12 and to the return electrode 16 can be via a wired connection (e.g., via a percutaneous wire or a subcutaneous wire). In other instances, the coupling of the waveform generator 14 to the charge capacity-expanding SINE 12 and/or to the return electrode 16 can be via a wireless connection. In still other instances, the coupling of the waveform generator 14 to the charge capacity-expanding SINE 12 and/or to the return electrode 16 can be via a connection that is both wired and wireless.

The waveform generator 14 can generate an electrical neuromodulation signal to provide neuromodulation to one or more nerves. In some instances, the neuromodulation signal can be a voltage controlled or current controlled direct current (DC) waveform (with pulses that are anodic and/or cathodic). For example, the DC waveform can be constant level direct current waveform, a varying level direct current waveform, a direct current waveform followed by a recharge phase, a direct current waveform in combination with a high frequency signal, or the like. The DC waveform of the neuromodulation signal can have a sufficient amplitude to cause the nerve conduction block in a target neural structure. For example, the target neural structure can include one or more nerves.

Accordingly, the waveform generator 14 can be any device configured or programmed to generate the specified DC waveform for application to the target neural tissue to achieve an alternation in conduction thereof. The waveform generator 14 can be housed in the patient's body or outside the patient's body. One example of a waveform generator 14 is a battery-powered, portable generator (the waveform generator 14 positioned externally). Another example of a waveform generator 14 is an implantable generator (IPG) (at least a portion of the waveform generator 14 positioned subcutaneously). It will be appreciated that the waveform generator 14 can include additional components to selectively configure the DC waveform, such as an amplitude modulator (not shown).

The charge capacity-expanding SINE 12 can be coupled to the waveform generator 14 to receive the electrical neuromodulation modulation signal. The charge capacity-expanding SINE 12 can convert the electrical neuromodulation signal to an ionic neuromodulation signal that is delivered to one or more nerves. Accordingly, the charge-capacity-enhancing SINE The return electrode 16 can deliver the current back to the waveform generator 14. The return electrode 16 can be placed on the subject's skin or inside the body. The return electrode 16 must be stable and of sufficient capacity to not cause tissue damage. As an example, the return electrode 16 can be a geometrically large electrode and/or a high capacitance electrode. Examples of return electrode include a needle, a conductive sticky pad, or another charge capacity-expanding SINE electrode.

Figure 2:
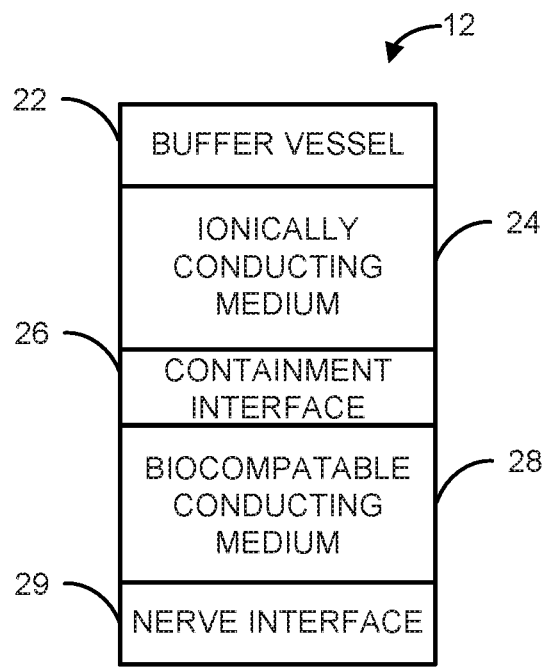
FIG. 2 is a diagram showing an example configuration of the charge capacity-expanding SINE in FIG. 1.

In some instances, the waveform generator 14 can be outside the subject's body. The return electrode 16 can be outside the subject's body, within the subject's body, or part outside and part inside the subject body. The charge capacity-expanding SINE 12 can be part outside the subject's body and part inside the subject's body. As shown in FIG. 2, the charge capacity-expanding SINE 12 can include a buffer vessel 22, a containment interface 26, and a nerve interface 29, as well as tubing to hold an ionically conducting medium 24 and a biocompatible conducting medium 28. In this example, the buffer vessel 22 can be outside the subject's body, while the ionically conducting medium 24 and the associated tubing, and the containment interface 26 may be inside or outside the subject's body. The biocompatible conducting medium 28 can be inside the subject's body. The nerve interface 29 can be inside the subject's body or transcutaneous. Additionally, in some instances, the nerve interface 29 can be positioned within the subject's body using an insertion tool (not shown). The insertion tool can be, for example, a special tip/tube to maximize the ability to place the nerve interface 29 in a desired location next to a nerve with minimal surgical effort. Alternatively, ultrasound can be used to guide the nerve interface 29 into position.

Figure 3:
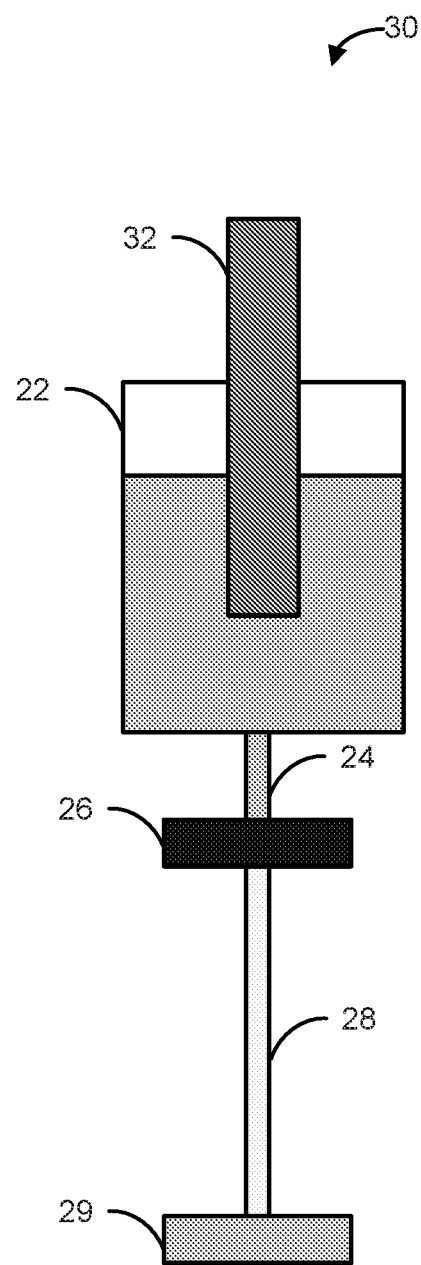
FIG. 3 is a schematic diagram showing an example of the charge capacity-expanding SINE in FIG. 1.

As shown in FIG. 3, the buffer vessel 22 can house a source electrode 32 and an ionically conducting medium 24. The ionically conducting medium 24 can be a medium (like saline, high conductance saline, a conductive gel, or the like) that could be biocompatible, but biocompatibility is not strictly necessary, which include a material that can facilitate conversion of the electrical neuromodulation signal to the ionic neuromodulation signal. The conversion can be according to a non-Faradaic process or a Faradaic process.

The non-Faradaic process occurs when the source electrode 32 placed in the ionically conducting medium 24 is a high capacitance electrode. In the non-Faradaic mode, no reactants are consumed and no reaction products are produced through the range of usage parameters defined by the particular electrical neuromodulation waveform. The material within the ionically conducting medium 24 can be in a solid piece or dispersed within the ionically conducting medium 24. The material can experience surface phenomena (double layer capacitance, like activated carbon), surface phenomena that involves specific adsorption (pseodocapacitance, like H adsorption on Pt), or bulk phenomena (like $IrO_2$, $MnO_2$, or $RuO_2$). For example, the ionically conducting medium 24 can be carbon slurry—a slurry of ionically conductive material with electrically conducting high surface area carbon particles. Volume fractions of ionic and electronic conducting material can be optimized to provide low resistance ionic and electronic pathways to a larger volume of material to maximize available capacitance. Other capacitive materials can be used to replace or in conjunction with the high surface area carbon. As another example, platinum black coated foil can be placed in saline to form the ionically conducting medium 24.

The Faradaic process occurs when the source electrode 32 is a redox active electrode placed in the ionically conducting medium 24. In this mode, redox reactions occur, but the medium is of sufficient volume to prevent pH changes at the nerve/electrode interface. Ideally, the redox reaction involves the uptake/discharge shuttle of biocompatible ions, like Na+, K+, or Cl—, to minimize or prevent any pH change or introduction of foreign ions. Redox reactions should be reversible to allow for recharge/reuse. The material used for redox can be insoluble to minimize any possible contamination of the subject. Redox reactions involving Na+ or K+ and an insoluble redox active material can include redox active polymers incorporating a polymeric anion (polypropyrrole with poly styrene sulfonate anion incorporated) or Prussian Blue (ferri-ferro hexacyanide). Redox reactions involving Cl—and an insoluble redox active material can include silver/silver chloride or redox active polymers, like polypyrrole, PEDOT, and the like.

The charge capacity-expanding SINE 12 includes a containment interface 26 that separates the ionically conducting medium 24 from a biocompatible conducting medium 28 and a nerve interface 29. The containment interface 26 allows ionic conduction, but prevents bulk flow a liquid electrolyte. Accordingly, the containment interface 26 prevents particulate migration into the biocompatible conducting medium 28. For example, the containment interface 26 can include a filter, a porous membrane, a viscous medium, a non-porous membrane, and/or a porous hydrophilic ceramic body. The biocompatible conducting medium 28 can be, for example, saline or a biocompatible gel.

The nerve interface 29 can allow for ionic current flow and include special features to maximize the efficacy of the DC block. For example, the nerve interface 29 can be a cuff to define/control current flow over the nerve. The cuff can be expandable and/or self-curling after insertion. As another example, the nerve interface 29 can be a percutaneous interface that uses different designs for alignment—such as parallel or perpendicular to a nerve. In another example, the nerve interface 29 can be a transcutaneous interface to interface to the patient's skin.

IV. METHODS

Figure 4:
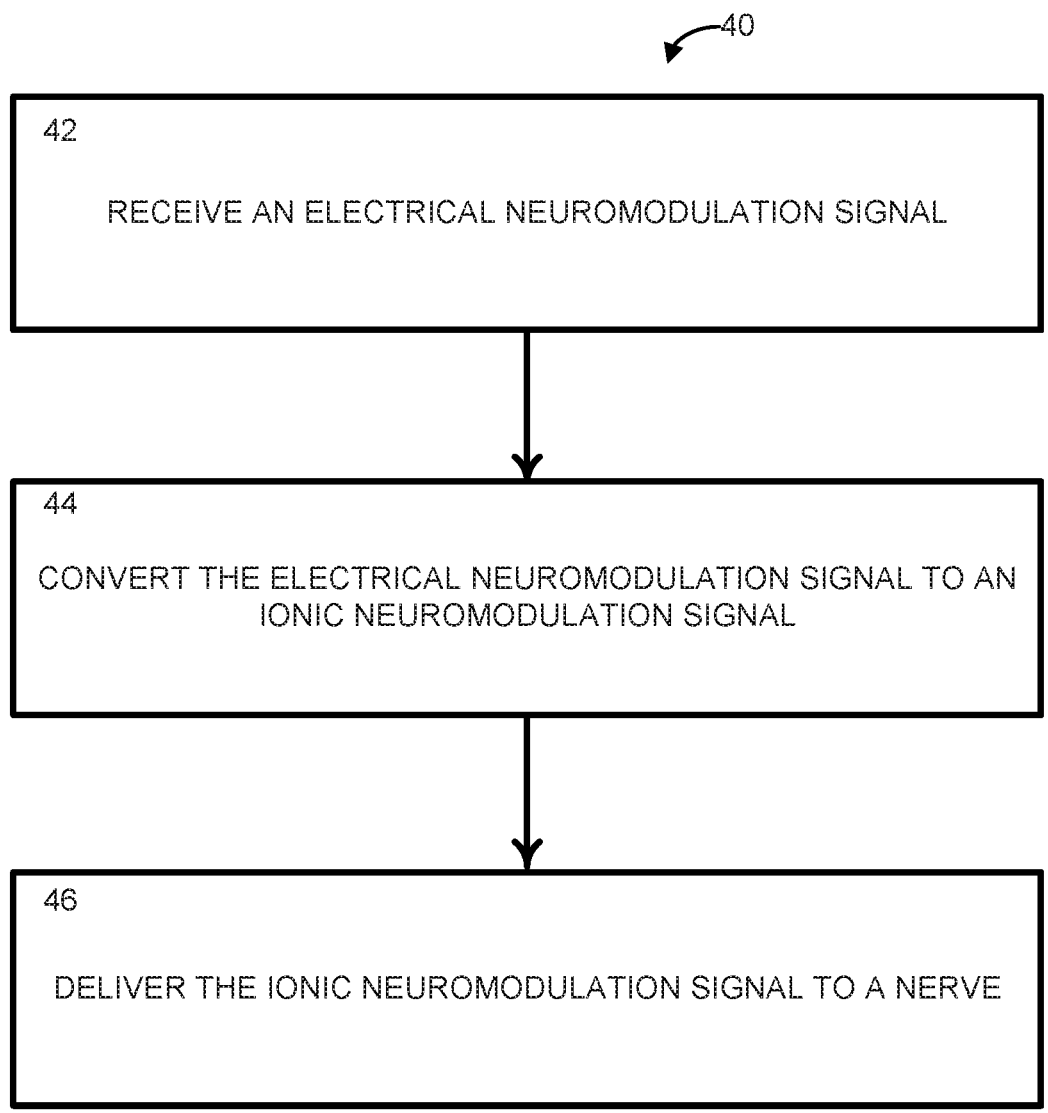
FIG. 4 is a process flow diagram illustrating a method for delivering a nerve conduction block to one or more nerves via the charge capacity-expanding SINE according to another aspect of the present disclosure.

Another aspect of the present disclosure can include a method 40 (FIG. 4) for delivering a nerve conduction block to one or more nerves via the charge capacity-expanding separated interface nerve electrode (SINE). The method 40 can be executed using the system 10 shown in FIG. 1 and described above using the charge capacity-enhanced SINE shown in FIGS. 2 and 3.

The method 40 can generally include the steps of: receiving an electrical neuromodulation signal (Step 42); converting the electrical neuromodulation signal to an ionic neuromodulation signal (Step 44); and delivering the ionic neuromodulation signal to a nerve (Step 46). The method 40 is illustrated as process flow diagrams with flowchart illustrations. For purposes of simplicity, the method 40 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 40.

At Step 42, an electrical neuromodulation signal (e.g., from waveform generator 14) can be received (e.g., by a source electrode 32 of the charge capacity-expanding SINE 12, 30). In other words, the electrical neuromodulation signal can be a direct current (DC) waveform generated by the waveform generator 14. For example, the DC waveform can be constant level direct current waveform, a varying level direct current waveform, a direct current waveform followed by a recharge phase, a direct current waveform in combination with a high frequency signal, or the like. The DC waveform can be either current controlled or voltage controlled.

At Step 44, the electrical neuromodulation signal can be converted to an ionic neuromodulation signal (e.g., in ionically conducting medium 24). The charge capacity-expanding SINE 12, 30 can include a source electrode 32 that can deliver the electrical neuromodulation signal to an ionically conducting medium 24 stored in a buffer vessel 22. The ionically conducting medium 24 can include a material that can facilitate the conversion of the electrical neuromodulation signal to the ionic neuromodulation signal.

In some instances, the conversion can be according to a non-Faradaic processes with a high capacitance electrode (e.g., source electrode 32) in the ionically conducting medium 24 that includes a material that facilitates the conversion of the electrical neuromodulation signal to the ionic neuromodulation signal. In the non-Faradaic process, no reactants are consumed and no reaction products are produced through a range of usage parameters as defined by the electrical neuromodulation signal. In these instances, the material is insoluble/non-corroding to minimize any possible contamination. The material may be in a solid piece or dispersed in the ionically conducting medium 24. For example, the material can be electrically conductive high surface area carbon particles that can be mixed into a slurry. As another example, the material can be platinum black coated foil. In either example, the material can be placed within saline to form the ionically conducting medium 24.

In other instances, the conversion can be according to a Faradaic process where redox reactions occur, but the medium is of sufficient volume to prevent pH change sat the nerve/electrode interface. The redox reactions should be reversible to allow for recharge/reuse. Additionally, the redox material should be insoluble to minimize any possible contamination of the subject. Examples of the redox material can include redox active polymers, Prussian Blue, or silver/silver chloride.

At Step 46, the ionic neuromodulation signal can be delivered to a nerve (e.g., through nerve interface 29). In some instances, the charge capacity-enhancing SINE can include a containment interface 26 to separate the ionically conducting medium 24 (or the material of the ionically conducting medium 24) from a biocompatible conducting medium 28, which can deliver the ionic neuromodulation signal to the nerve interface 29 and eventually the nerve. As an example, the nerve interface can be a nerve cuff, a percutaneous device aligned perpendicular to the nerve, a percutaneous device aligned parallel to the nerve, or a transcutaneous device. In some examples, the nerve can be a peripheral nerve or neural fibers (e.g., motor, sensory, enteric, and/or autonomic) or a nerve or nervous tissue comprising the central nervous system (e.g., brain and/or spinal cord). It should be noted that the current is returned back to the waveform generator 14 after delivery to the nerve by a return electrode 16.

V. EXPERIMENTAL

A charge capacity-enhanced separated interface nerve electrode (SINE) can be used in a variety of block applications, as shown in the following experiments. The following experimental results are shown for the purpose of illustration only and are not intended to limit the scope of the appended claims.

The charge capacity-expanding SINE 30 used in the following experiments was configured as shown in FIG. 3 and attached to a waveform generator. A return electrode was also attached to the waveform generator. To establish nerve block using a DC waveform, a current on the order of 1 mA for up to 20 seconds may be required. Thus, the total electrical charge passed is ≈20 mC. This charge can be delivered via either a Faradaic (i.e., an electrochemical reaction) process or a non-Faradaic process (charging/discharging of the electrochemical double layer capacitance). Given the relatively small amount of charge required, a non-Faradaic source electrode would be feasible and preferable. It is well known that carbon-based materials can be formed with extremely high levels of porosity. The result is that these materials have very high surface areas (values exceeding 1,000 $m^2$ of surface area/gram of carbon are not uncommon). When placed in an electrolyte solution, the electrochemical capacitance of the materials is then on the order of 100-200 F/g. Thus, a very small amount of material can store a significant amount of electrical charge. If the capacitance is normalized to the apparent area of the electrode (that is, the electrode's surface area calculated from its gross dimensions of width and length), the capacitance is on the order of 100-500 $mF/cm^2$. This property is basis for the commercial production of electrochemical double layer capacitors (EDLCs), also known as super- or ultra-capacitors, which are available from a number of manufacturers. The carbons used in these capacitors are typically produced by the pyrolysis of coconut shells, and are non-toxic. Since the charging and discharging mechanism involves only the motion of ions in the electrolytes and electrons within the carbon, these capacitors routinely can be charged and discharged over 100,000 times. Assume a relatively small voltage change of 0.5V between the charged and discharged states of the capacitor, a capacitance of 40 mF would be sufficient to provide the 20 mC charge required. A 1 mm dia wire, 1 cm long, coated with a typical EDLC carbon electrode having an area specific capacitance of 350 $mF/cm^2$, would have a capacitance of 100 mF—easily meeting our requirement for charge storage in a small volume. The charge/discharge process should be highly reproducible, and would not introduce any foreign ions into the electrolyte or change the electrolyte pH.

The source electrode 32 (or current collector) was a corrosion-resistant graphite rod (⅛" dia), inserted through a one hole stopper in the top of a syringe. The buffer vessel 22 was a 10 cc syringe partially filled with carbon paste. The carbon paste included high surface area carbon (YP-50) added to saline. The carbon paste formed the ionically conducting medium 24. All of the carbon in the paste was electrochemically available for capacitive (double-layer) charging. The paste was concentrated enough so that it was both electrically conductive and ionically conductive. All carbon particles in the solution were electrically connected together, and the solution was ionically continuous.

The containment interface 26 used in this experiment was a Luer Lock syringe filter, 0.45 μm. The syringe filter prevents the carbon from leaching out into the electrolyte connection down to the nerve. The biocompatible conducting medium 28 can include an electrolyte, which was saline in this example. The saline can be housed in tubing until reaching the nerve interface 29. The nerve interface 29 can be a nerve cuff and/or a percutaneous delivery device. The charge capacity-expanding SINE 30 can be pre-charged to a 1 volt difference to optimize the charge capacity (~600 C or 7 days at 1 mA).

Figure 5:
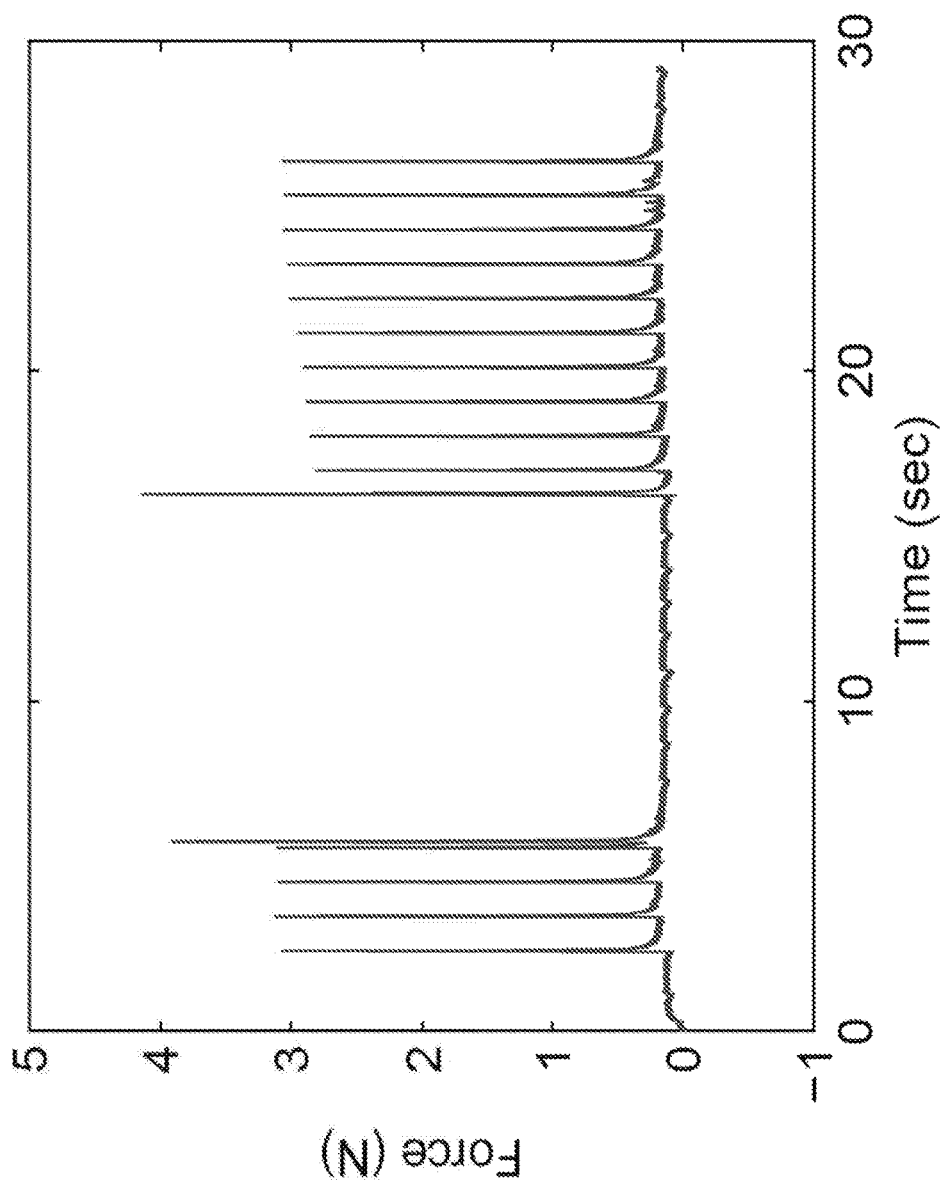
FIG. 5 is a plot showing a complete block at −1.0 mA using a carbon filled SINE cuff electrode.

The charge capacity-expanding SINE 30 can have a nerve interface 29 in the form of a nerve cuff. The charge capacity-expanding SINE 30 can be used to achieve a complete block or a partial block. A complete block at −1.0 mA was achieved as shown in FIG. 5, while a 75% block was achieved at −0.1 mA as shown in FIG. 6.

The charge capacity-expanding SINE 30 can have a nerve interface 29 in the form of a percutaneous electrode. As shown in FIGS. 7-9, complete block can be achieved at different current levels (−1.6 mA in FIG. 7, −1.2 mA in FIG. 8, and −1.0 mA in FIG. 9). As the current level is reduced, the effect takes longer to be established. This phenomenon can be used to reduce the power requirements of the system if longer block initiation times are acceptable.

Figure 10:
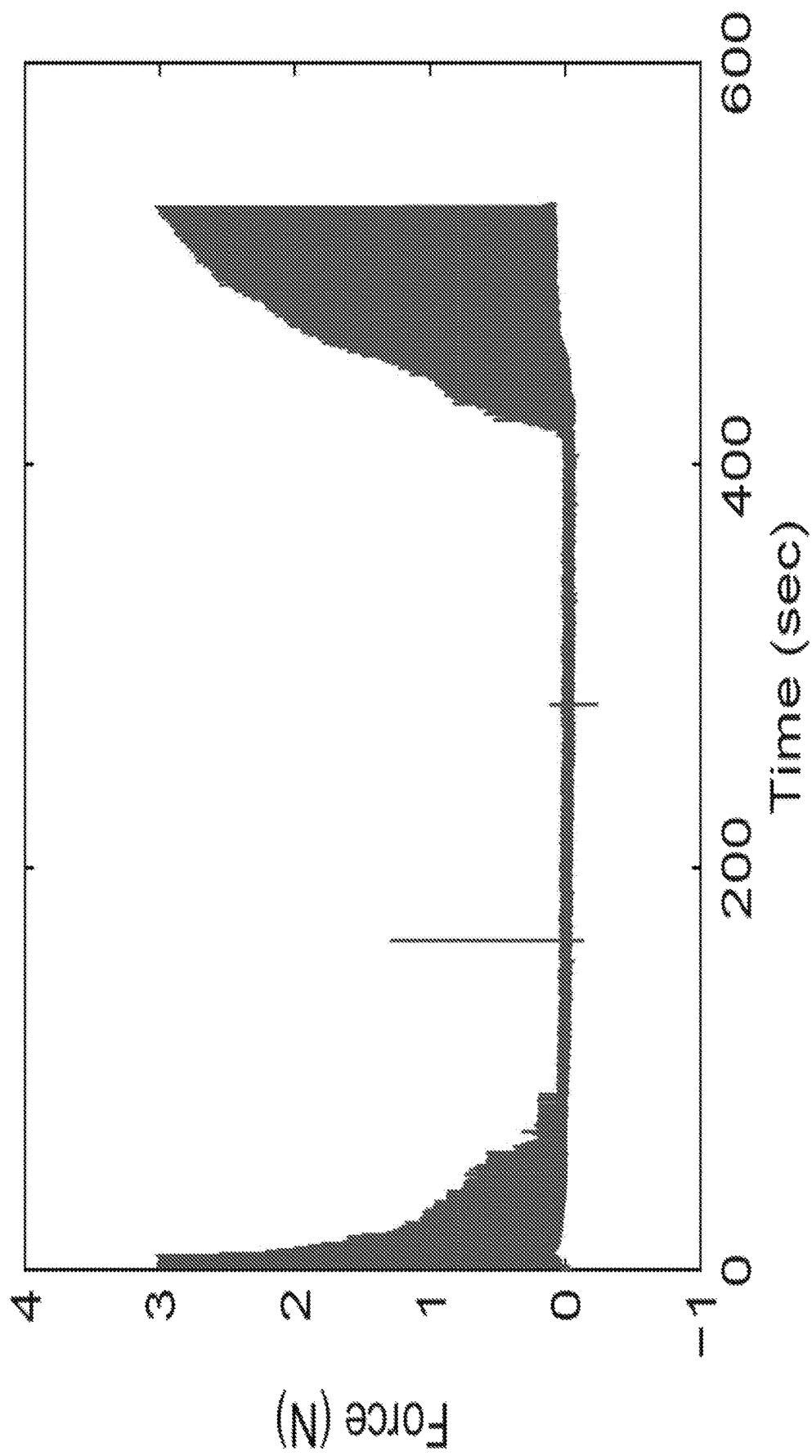
FIG. 10 is a plot showing complete block at −1.2 mA after 50 seconds using a carbon filled SINE cuff electrode.
Figure 11:
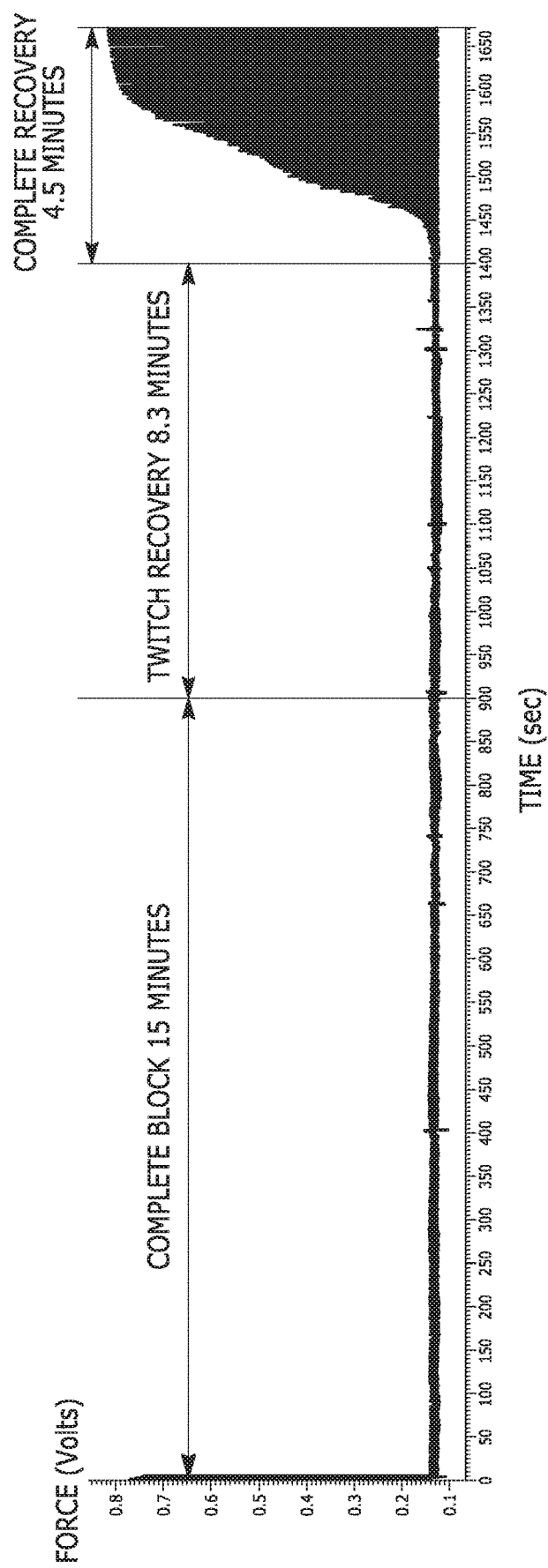
FIG. 11 is a plot showing complete block achieved for 15 minutes using a using a carbon filled SINE cuff electrode.

The charge capacity-expanding SINE 30 as having a nerve interface 29 in the form of a cuff electrode. FIG. 10 shows complete block being established at −1.2 mA after 50 seconds. The initiation time was shown to be repeatable. It is possible that the initiation can be achieved more quickly with higher levels of block. Moreover, as shown in FIG. 10, the complete block was maintained for 5 minutes, while complete recovery was achieved in 100 seconds. FIG. 11 shows complete block being maintained for 15 minutes, twitch recovery was shown to last 8.3 minutes, while complete recovery was established 4.5 minutes thereafter.

VI. EXAMPLES

Direct current (DC) nerve conduction block is fast acting, reversible, onset free, and easy to modulate, making it ideal for a variety of applications in a patient's nervous system. However, DC can deliver negative side effects to a patient's body. Accordingly, the DC can be delivered to a charge capacity-expanding separated interface nerve electrode (SINE), which can provide a polarizing current nerve block, while separating any potentially damaging reagents from the nerve. It will be appreciated that DC nerve conduction block can be applied through a charge capacity-enhanced SINE to one or more neural structures related to the central nervous system, peripheral nervous system, autonomic nervous system, and enteric nervous system. Described below are certain examples of some of the various medical conditions for which DC nerve conduction block can be applied through a charge capacity-enhanced SINE. The following examples are not meant to be limiting.

Motor System

In the motor system, spasticity is a debilitating condition that is a result of many different neurological conditions. A few examples of such neurological conditions include cerebral palsy, multiple sclerosis, spinal cord injury and stroke. In each example, the onset of spasticity results in many impairments and limitations including, but not limited to, gait disorders, fatigue, restricted range of movement, abnormal limb postures, quality of life issues, problems with activities of daily living, and/or pain, all of which impact the patient's quality of life. In addition to the quality of life impact of spasticity, the economic burden of any neurological condition increases significantly at the onset of spasticity. For stroke, it has been demonstrated that spasticity causes a four-fold increase in the direct costs associated with treating stroke patients. DC nerve conduction block can be applied through a charge capacity-enhanced SINE and modulated to provide a solution that can minimize spasticity while maintaining muscle tone allowing for previously unattainable functional improvements.

Sensory System

In the sensory system, chronic neuropathic pain would be an ideal target for DC nerve conduction block that can be applied through a charge capacity-enhanced SINE. Neuropathic pain follows trauma or disease affecting the peripheral or central nervous system. Examples of such trauma can include physical trauma, spinal cord injury, while examples of such disease can be a side effect of chemotherapy, radiation, or surgery.

With some peripheral neuropathic pain, the source of the pain is localized at a neuroma. As is common with amputations, when a peripheral nerve is damaged, the peripheral nerve tries to regenerate itself towards the distal target. If the distal target is unavailable, axon sprouts grow into the surrounding scar tissue forming a neuroma, which can cause chronic pain and hypersensitivity. A neuroma is particularly well suited to DC nerve conduction block that can be applied through a charge capacity-enhanced SINE given the local nature of the condition. Also, with DC nerve conduction block that can be applied through a charge capacity-enhanced SINE, the nerve interface can easily be removed and placed in a different location, making the charge capacity-enhanced SINE desirable in the event that the neuroma changes in a way that lessens the effect of the nerve block.

Autonomic System

In the autonomic system, the properties of DC nerve conduction block applied through a charge capacity-enhanced SINE provide a unique opportunity for modulation of neural activity. The autonomic nervous system frequently operates around a baseline of neural activity, which is modulated up or down to produce the desired physiological effects. For example, blood pressure is maintained through tonic activity in the autonomic nervous system. It would be extremely beneficial to not only be able to enhance neural activity, but also to inhibit neural activity in a graded/modulated manner Direct current can be modulated to affect a sub-population of axons to achieve a graded response. In the autonomic system, the onset response is particularly confounding since the effect is prolonged due to the dynamics of the system. The ability to produce an onset free nerve block is absolutely critical to provide an effective solution to autonomic diseases, and the nature of the DC nerve conduction block applied through a charge capacity-enhanced SINE leads to greater use of the block throughout the medical community.

Regional Applications

Some regional applications are well suited to DC nerve conduction block that can be applied through a charge capacity-enhanced SINE. As an example, damage to the occipital nerve can result in chronic headache symptoms. Pharmacological nerve blocks, which are often used to treat this condition, could easily be replaced with a DC nerve conduction block that can be applied through a charge capacity-enhanced SINE, which would provide a longer-term relief. As another example, the pudendal nerve has successfully been blocked using KHFAC and nerve cuff electrodes for bladder control. Both of these methods could be enhanced by DC nerve conduction block that can be applied through a charge capacity-enhanced SINE. Also, the DC administered through the charge capacity-enhanced SINE would be capable of providing smooth transitions between partial and complete block which could further improve the functionality of the application.

From the above description, those skilled in the art will perceive improvements, changes and modifications. Such improvements, changes and modifications are within the skill of one in the art and are intended to be covered by the appended claims.

The following is claimed:

1. A system comprising:
   a waveform generator configured to output an electrical neuromodulation signal;
   a separated interface nerve electrode comprising:
      a source electrode coupled to the waveform generator configured to deliver the electrical neuromodulation signal to an ionically conducting medium
      wherein the ionically conducting medium comprises a slurry of a first material and a second material that is both electrically conductive and ionically conducting, wherein the second material includes a high surface area material adapted for capacitive charging to facilitate a transformation of the electrical neuromodulation signal to an ionic neuromodulation signal; and
      a nerve interface configured to contact the nerve and deliver the ionic neuromodulation signal to the nerve; and
   a return electrode coupled to the waveform generator.

2. The system of claim 1, wherein the ionically conducting medium facilitates a faradaic reaction or a non-faradaic reaction with the source electrode to transform the electrical neuromodulation signal to the ionic neuromodulation signal.

3. The system of claim 1, wherein the second material comprises high surface area carbon.

4. The system of claim 3, wherein the first material comprises saline.

5. The system of claim 1, wherein the second material comprises a charge transfer material to facilitate a redox reaction.

6. The system of claim 1 further comprising:
   a buffer vessel encapsulating at least a portion of the source electrode to receive the electrical neuromodulation signal, wherein the buffer vessel comprises the ionically conducting medium;
   a biocompatible vessel encapsulating a biocompatible conducting medium to conduct the ionic neuromodulation signal to the nerve interface; and a biocompatible containment interface separating the ionically conducting medium and the biocompatible conducting medium, wherein the biocompatible containment interface is configured to prevent the material from the ionically conducting medium from entering the biocompatible ionically conducting medium.

7. The system of claim 6, wherein the biocompatible containment interface comprises at least one of a filter, a porous membrane, a viscous membrane, a non-porous membrane, a solid body of an ion-exchange polymer, or a porous hydrophilic ceramic body.

8. The system of claim 1, wherein the electrical neuromodulation signal comprises a constant level direct current waveform, a varying level direct current waveform, a direct current waveform followed by a recharge phase, or a direct current waveform in combination with a high frequency signal.

9. The system of claim 1, wherein the nerve interface comprises a cuff, a percutaneous device aligned perpendicular to the nerve, a percutaneous device aligned parallel to the nerve, or a transcutaneous device.

10. The system of claim 1, wherein the electrical neural modulation signal is configured to provide a partial nerve block.

11. The system of claim 1, wherein the return electrode is a geometrically large electrode or a high capacitance electrode.

12. The system of claim 1, further comprising an insertion tool configured to facilitate placement of the nerve interface to a defined position proximal to the nerve.

13. The system of claim 6, wherein the nerve interface and at least a portion of the vessel are configured for insertion into a patient's body.

14. A method comprising:
outputting an electrical neuromodulation signal by a waveform generator to a separated interface nerve electrode;
converting, by the separated interface nerve electrode, the electrical neuromodulation signal to an ionic neuromodulation signal, wherein the separated nerve interface electrode comprises a source electrode configured to deliver the electrical neuromodulation signal into an ionically conductive medium, wherein the ionically conducting medium comprises a slurry of a first material and a second material that is both electrically conductive and ionically conducting, wherein the second material includes a high surface area material adapted for capacitive charging to facilitate the conversion of the electrical neuromodulation signal to the ionic neuromodulation signal; and
delivering, by a nerve interface configured to contact a nerve, the ionic neuromodulation signal to the nerve.

15. The method of claim 14, wherein the ionically conducting medium facilitates a faradaic reaction or a non-faradaic reaction with the source electrode to transform the electrical neuromodulation signal to the ionic neuromodulation signal.

16. The method of claim 14, wherein the second material comprises high surface area carbon.

17. The method of claim 16, wherein the first material comprises saline.

18. The method of claim 16, wherein the second material comprises a charge transfer material to facilitate a redox reaction.

19. The method of claim 16, wherein the nerve interface comprises a cuff, a percutaneous device aligned perpendicular to the nerve, a percutaneous device aligned parallel to the nerve, or a transcutaneous device.

20. The method of claim 16, wherein the electrical neuromodulation signal comprises a constant level direct current waveform, a varying level direct current waveform, a direct current waveform followed by a recharge phase, or a direct current waveform in combination with a high frequency signal.

* * * * *